United States Patent [19]

Montalbano

[11] 4,441,494
[45] Apr. 10, 1984

[54] COLD WEATHER BREATHING DEVICE

[76] Inventor: Anthony P. Montalbano, 29 Hitching Post La., Glen Cove, N.Y. 11542

[21] Appl. No.: 239,497

[22] Filed: Mar. 2, 1981

[51] Int. Cl.³ .......................................... A61M 16/00
[52] U.S. Cl. ............................. 128/204.17; 128/207.16
[58] Field of Search .................... 128/201.13, 204.17, 128/202.26, 205.12, 205.25, 207.12, 207.16

[56] References Cited

U.S. PATENT DOCUMENTS

| | | |
|---|---|---|
| 443,191 | 12/1890 | Illing . |
| 603,021 | 4/1898 | Dight . |
| 1,880,998 | 10/1932 | Sturtevant ...................... 128/207.16 |
| 2,348,108 | 5/1944 | Bulbulian . |
| 2,468,383 | 4/1949 | Tiffany . |
| 2,610,038 | 9/1952 | Phillips . |
| 2,647,511 | 8/1953 | Barach ........................... 128/204.25 |
| 3,037,501 | 6/1962 | Miller . |
| 3,107,669 | 10/1963 | Gross . |
| 3,249,108 | 5/1966 | Terman . |
| 3,265,060 | 3/1964 | Schreiber . |
| 3,326,214 | 6/1967 | McCoy . |
| 3,348,540 | 10/1967 | Cullity . |
| 3,357,424 | 12/1967 | Schreiber . |
| 3,491,754 | 1/1970 | Weese . |
| 3,669,109 | 6/1972 | Cheffers . |
| 3,707,966 | 1/1973 | Nebel ............................. 128/204.17 |
| 3,747,598 | 7/1973 | Cowans . |
| 3,814,094 | 6/1974 | De Angelis et al. . |
| 3,827,440 | 8/1974 | Birch et al. . |
| 3,844,290 | 10/1974 | Birch et al. . |
| 3,908,649 | 9/1975 | Eckstein . |
| 4,030,493 | 6/1977 | Walters et al. . |
| 4,050,466 | 9/1977 | Koerbacher . |
| 4,062,359 | 12/1977 | Geaghan . |
| 4,150,671 | 4/1979 | Tiger . |
| 4,196,728 | 4/1980 | Granite . |
| 4,222,378 | 9/1980 | Mahoney . |
| 4,245,631 | 1/1981 | Wilkinson et al. . |

FOREIGN PATENT DOCUMENTS

| | | |
|---|---|---|
| 21424 | 6/1882 | Fed. Rep. of Germany . |
| 520342 | 6/1921 | Fed. Rep. of Germany ...................... 128/206.22 |

OTHER PUBLICATIONS

"Respiratory Therapy", Dennis W. Glover, Margaret McCarthy Glover, C. W. Mosby Company, Saint Louis, 1978, p. 19.

Primary Examiner—Henry J. Recla
Attorney, Agent, or Firm—Frishauf, Holtz, Goodman & Woodward

[57] ABSTRACT

A cold weather breathing device comprises a mouthpiece, a valve unit containing first and second valves in air communication with the mouthpiece and a conduit (preferably flexible) extending downwardly from the valve unit. The first valve in the valve unit provides air communication between the conduit and the mouthpiece when the user inhales, and blocks said air communication when the user exhales. A second valve in the valve unit provides air communication between the mouthpiece and an exhaust opening of the valve unit when the user exhales, and for blocking such air communication when the user inhales. Further provided is a shield unit including a substantially air impervious member coupled to an end of the conduit remote from the mouthpiece, and a plurality of projections extending from the air impervious member for spacing the air impervious member from a body portion of the user so as to provide at least one air passage between the air impervious member and the surface of the user against which the projections are adjacent, the at least one air passage being in air communication with the interior of the conduit. In this manner, body heat is used to effectively heat the air being inhaled by the user via the air passage(s), conduit and valve unit.

21 Claims, 5 Drawing Figures

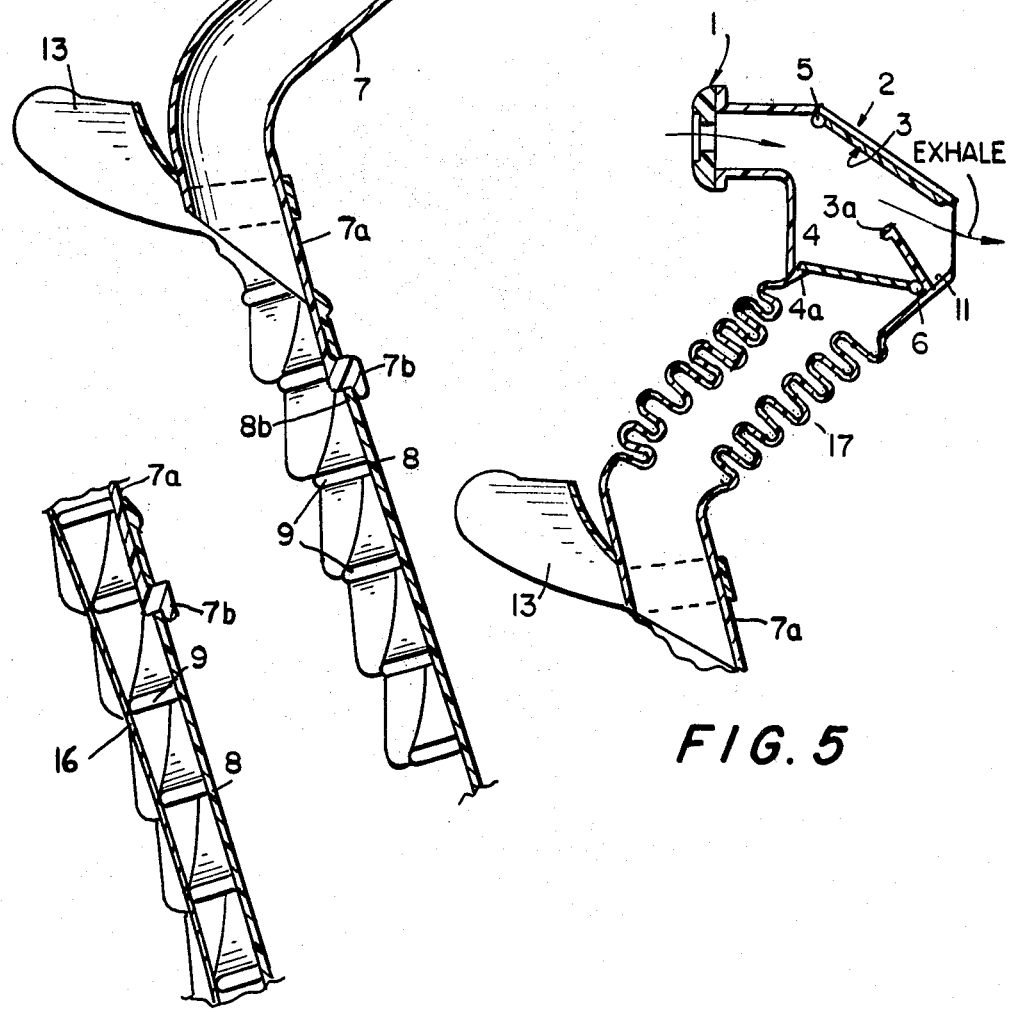

COLD WEATHER BREATHING DEVICE

BACKGROUND OF THE INVENTION

This invention relates to a cold weather breathing device, and more particularly to such a device which uses body heat to heat the air being inhaled by the user.

When walking, jogging, running, hunting or carrying out other physical activity in cold weather, one generally has a great deal of discomfort due to the breathing in of very cold air. Additionally, medical problems may be caused due to breathing in cold air when performing physical activities.

The object of the present invention is to provide a simplified cold air breathing device which uses body heat to heat the inhaled air, and which is easy to manufacture, easy to use, simple in construction, highly reliable and rugged.

A further object is to provide such a device which also moisturizes the air being inhaled.

Yet another object is to enable the rebreathing of the bi-product of the user's body heat so that normal warm body temperatures can be maintained while burning less energy.

Still another object is to provide such a device which enables substantially complete mobility of the head of a user, for safety purposes.

SUMMARY OF THE INVENTION

According to the present invention, a cold weather breathing device comprises a mouthpiece which does not extend to the nose of a user and which is insertable in the mouth of the user and substantially provides a seal to the mouth of the user; a conduit extending downwardly from the mouthpiece and in selective air communication with the mouthpiece; a first valve in air communication with the conduit and mouthpiece for providing an air communication path between the conduit and mouthpiece when the user inhales, and for blocking the air communication path between the conduit and mouthpiece when the user exhales; and exhaust opening coupled to the mouthpiece for selectively exhausting exhaled air to the atmosphere; a second valve coupled between the exhaust opening and the mouthpiece for providing an air communication path between the mouthpiece and the exhaust opening when the user exhales, and for blocking the air communication path between the exhaust opening and mouthpiece when the user inhales; and a shield unit including a substantially air impervious member coupled to an end portion of the conduit remote from the mouthpiece, and a plurality of projections extending from the air impervious member for spacing the air impervious member from a body portion of the user so as to provide at least one air passage between the air impervious member and the body surface of the user against which the projections are adjacent, the at least one air passage being in air communication with the interior of the conduit.

BRIEF DESCRIPTION OF THE DRAWINGS

FIG. 3 is a part-sectional side view along the line 3—3 in FIG. 1 showing the valves in the exhale position;

FIG. 4 is a sectional view showing details of the lower portion of the device, and showing a modification; and FIG. 5 is a partial sectional view showing a modified embodiment of the present invention.

DETAILED DESCRIPTION

Figures 1, 2:
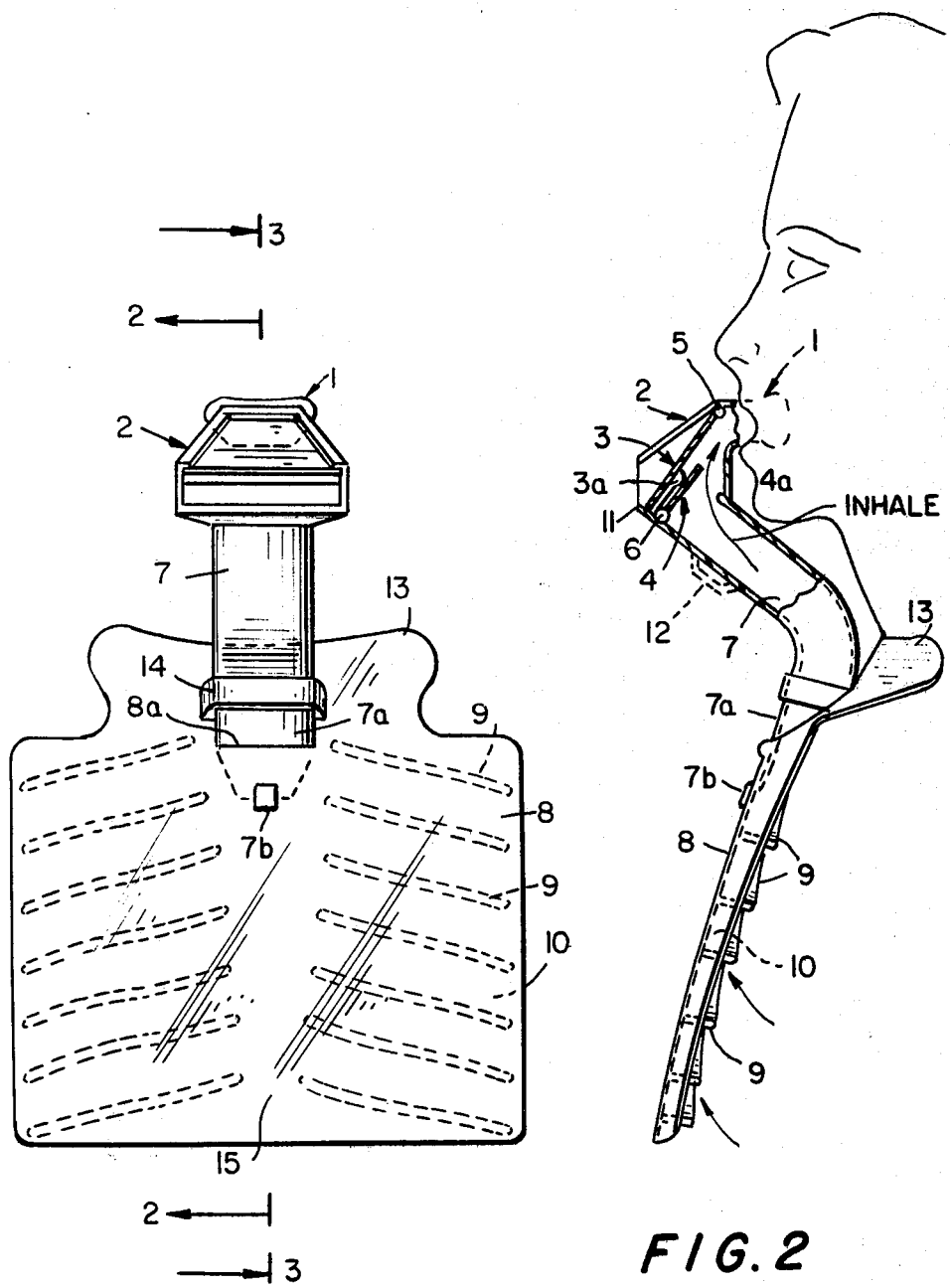
FIG. 1 is a front view of the device of the present invention.
FIG. 2 is a side, part-sectional view of the device of FIG. 1, in use, showng the valves in the whole position.

Referring to FIGS. 1–3, the illustrated device of the present invention enables a person to breathe warm air at temperatures above those present in the surrounding cold ambient air.

The device of the present invention comprises a mouthpiece 1 and a valve housing section 2 connected to the mouthpiece 1. The valve housing 2 comprises a flap-type exhaust valve plate 3 and an associated seat 3a. The valve housing 2 further includes a flap-type intake valve plate 4 and an associated seat 4a. Flap valve 4 pivots about a pivot pin 6 between seat 4a and seat 3a (which serves as a stop for flap valve 4). Flap-valve 3 pivots about a pivot pin 5 between the open (exhale) position shown in FIG. 3 and the closed (inhale) position shown in FIG. 2. Flap-valve 4 pivots between the closed (exhale) position shown in FIG. 3, and the open (inhale) position shown in FIG. 2). A conduit 7 is coupled to the valve housing 2 and extends down to a shield unit 8 which includes a substantially air impervious shield member 8 which is maintained spaced apart from the chest of the wearer by means of ribs or projections 9 which extend rearwardly of the shield 8 to provide a plurality of passages 10 for air flow. The respective passages 10 are defined by the chest of the wearer, the inner surface of the shield 8, and the dividing ribs, spacers or projections 9. The conduit 7 is coupled to an end central portion of the shield 8, in an air-tight sealing relationship so that it is in air communication with the underside of the shield 8 and in air communication with the air flow passages 10 defined by the shield and body of the user. The lower flange 7a of conduit 7 extends through a holding member 14 which is connected to or integrally extending from the shield 8. Flange 7a then passes over a portion of the shield 8, through an opening 8a in shield 8, under shield 8, and a tab 7b extends outwardly through an opening 8b in shield 8 to lock the members together. Other methods may be used to attach conduit 7 to shield 8, for example an adhesive, rivets, screws, etc.

A saliva catch 11 is provided on the valve housing 2 as shown in FIGS. 2 and 3 to catch excess saliva contained in the exhaled air. A further saliva catch 12 is optionally provided in conduit 7 (see FIG. 2) to catch any excess saliva which may escape through valve 3. Further provided is a collar member 13, for extending from and being a part of shield 8, to seal the opening between the upper open end of the shield 8 and the outside environment, thereby preventing escape of heated air from behind the shield 8 and preventing cold drafts.

The conduit 7 is preferably made of flexible material so that the device may conform to all users. The collar 13 is preferably of resilient material so that it may conform to the user's body configuration and will provide proper sealing even when the shield 8 is in various different locations on the chest of the user.

For safety reasons it is desirable that conduit 7 be highly flexible so that the user may move his (her) head freely to view traffic or other hazards. In order to improve safety, the conduit 7 may comprise a flexible bellows unit 17 as illustrated in FIG. 5. The bellows may preferably be made of a rugged flexible material such as vinyl.

The device functions as follows: when a person draws a breath (inhales), the suction opens the one-way inlet valve 4 so that the flap 4 pivots upwardly to the position shown in FIG. 2, thereby permitting inhaling or drawing in of air through the flexible conduit 7 from the area between the undersurface of the shield 8 and the chest of the user. Natural radiant body heat is captivated and directed toward conduit 7 by the shield 8 which is maintained spaced from the body by means of longitudinal projections or ribs 9, and air drawn in through the channels 10 and central channel 15 is heated by the captivated heat. The outer surface of the shield 8 (preferably air impervious plastic) prevents body heat loss by affording an air insulating barrier between the body heat and the surrounding ambient air. The outer air impervious surface of shield 8 also prevents body heat loss and enables ribs 9 to direct and converge the heated air to the ingress of the flexible conduit 7. Ribs 9 also act as spacers to prevent ones outer garments from collapsing the air chamber between shield 8 and the body surface. The collar 13 is also an air flow barrier which prevents heat loss through the shirt or upper opening area of the device, and prevents cold drafts on the chest of the user. Thus, incoming fresh air drawn in through, for example, the pores of the person's clothing, openings between garment sections, etc., may be heated and inhaled. The inhaled air is also moisturized by the moisture given off by the body during the activity.

When the person exhales, the valve 4 closes and the exhaust valve 3 opens (FIG. 3). This releases the heated exhaled breath to the atmosphere. The intake valve 4 and the exhaust valve 3 are both one-way valves of the flap-type. Diaphragm or poppet-type valves can also be used.

The inherent attributes of this invention are as that it enables one to run, jog, walk, or do any other activity in cold ambient surroundings, while breathing warm, moist, fresh air regardless of the low surrounding atmospheric temperatures. The device has been tested at atmospheric ambients of 4° F. producing heated temperatures of approximately 70° F. internal. Another prime attribute of the device is that rebreathing the bi-products of ones body heat enables one to maintain normal warm body temperatures while burning less energy.

In severe cold temperatures, the shield 8 would be located under the outer garments worn over the upper torso area of the user. Valves 3 and 4 are large enough to permit a maximum exchange of air with little or no restriction to normal breathing, as well as to a stressed cycle when one is, for example, running or jogging. Moisture retained in the device while running or jogging humidifies the breathed-in air, thus preventing dry throat. Moreover, the moisture generated by perspiration in the chest area humidifies the air passing through passages 10, 15, thereby further preventing dry throat and increasing breathing comfort. Thus, not only is the incoming air warmed, it is also efficiently and effectively humidified. Still further, since the incoming air is drawn in preferably through the outer garment pores, openings, etc., the incoming air has had a chance to be somewhat heated while inside the garments, before passing through the air channels 10, 15 formed by the shield 8.

Preferably, the flexible tube 7 (or bellows 17) and the valve housing 2 are made of flexible vinyl material. The valve flaps or plates 3, 4 are also preferably made of a lightweight plastic material and are mounted to the valve housing by pivot pins or the like. When the pivot pins and valve flaps are properly designed, the valve flaps move between their opened and closed positions with very little or no resistance, thereby creating substantially no restriction to normal or stressed breathing.

In a modified arrangement shown in FIG. 4, a porous layer 16 such as fabric, can be located over the rear surfaces of ribs 9. Layer 16 may provide better comfort and aid in maintaining the device in position on the user's chest. The shield 8 may be strapped in place by means of straps (not shown) extending around the back of the user.

In any natural body breathing device (i.e., a snorkel tube), excessive length of tube and/or number of bends in the breathing tube will cause resistance to air flow. In particular, excess tube length is a critical problem in that breathing fatigue will result. This invention takes advantage of a very short breathing tube 7 with the air ingress opening close to the prime body heat radiating area, directly over the lungs.

This invention allows the user to directly breathe radiant heat generated from the body, thus eliminating the need for complex heat exchange tubes and devices which tend to restrict free air flow and add unnecessary bulk and weight to the device. Further, the device of the present invention exhausts directly into ambient air, thus eliminating any back pressure that would result from exhausting into a tube, sack or manifold. Such a back pressure would restrict breathing and would cause the body to work harder.

The present device is so designed as to be highly compact and portable, and will fit into any small bag or back pocket. It can be made of flexible plastic to make it even more convenient to use and carry.

The device of the invention preferably utilizes an oral mouthpiece only, thus restricting residue humidity and saliva to normally wet internal mouth and throat areas. Devices using nose and mouth mask may become totally saturated in use, thus making it very uncomfortable in low ambient temperatures. The mouthpiece (only) device minimizes rebreathing of exhausted air because the above mentioned nose and mouth mask presents a large chamber where partial exhausted air is rebreathed. Moreover, in the present invention, because of the close proximity and arrangement of the inlet and exhaust valves 3, 4, rebreathing of previously exhausted air is minimized.

The shield 8, with its spacing ribs 9, acts as an insulator and spacer device. Although simple in configuration, it performs the following functions:
a. The plastic outer surface of shield 8 prevents cold ambient air from reaching the chest through the outer garments.
b. The shield 8 also prevents body heat from radiating out through the outer garments.
c. Shield 8 directs air towards the ingress of tube 7.
d. Shield 8 affords an air space chamber to which radiant heat emitted from most of the entire chest area is drawn.

The device of the invention is designed to be used in cold winter ambients, such as 40° F. and lower. Therefore any normal outer garment can be worn, such as a T-shirt, sweat shirt, windbreaker or any combination of the above. An attribute of this device is that the longer one jogs or runs, the greater the BTU's emanating from the body, and thus passing through the device. This reclamation of previously wasted body heat enables one to easily maintain warm body temperatures even in sub-zero weather.

While the device has been described with respect to a preferred embodiment, various modifications can be made within the scope of the appended claims.

I claim:

1. A cold weather device comprising:
   a mouthpiece (1) which is engageable only with the mouth area of a user and which is insertable in the mouth of the user and substantially provides a seal to the mouth of the user, said mouthpiece not extending to the nose of the user and leaving the nose of the user uncovered;
   a valve housing (2) coupled to said mouthpiece (1) and in air communication with only the mouth of the user via said mouthpiece (1), and being out of air communication with the nose of the user;
   a conduit (7) extending downwardly from said valve housing (2) and in selective air communication with said mouthpiece (1) via said valve housing (2);
   a first valve (4) in said valve housing (2) and in air communication with said conduit (7) and mouthpiece (1) for providing an air communication path between said conduit and said mouthpiece when the user inhales, and for blocking said air communication path between said conduit and mouthpiece when the user exhales;
   an exhaust opening in said valve housing (2) and being in selective air communication with said mouthpiece (1) for selectively exhausting exhaled air to the atmosphere;
   a second valve (3) in said valve housing (2) and coupled between said exhaust opening and said mouthpiece (1) for providing an air communication path between said mouthpiece and said exhaust opening when the user exhales, and for blocking said air communication path between said exhaust opening and mouthpiece when the user inhales; and
   a shield unit having a top end, opposite sides, a bottom end and a substantially central portion, said shield unit including a substantially air impervious shield member (8) coupled to an end portion of said conduit (7) remote from said mouthpiece (1) and a first and second plurality of spaced apart projecting ribs (9) extending from one side of said shield member (8), adjacent ribs defining with said shield member (8) a plurality of elongated, generally U-shaped, substantially unrestricted air passage channels (10), said first plurality of ribs being on one side of said substantially central portion of said shield unit and said ribs of said first plurality of ribs having one end located adjacent the periphery of said shield member (8) and an opposite end located adjacent said substantially central portion of said shield member, said second plurality of ribs being on the other side of said substantially central portion of said shield unit and said ribs of said second plurality of ribs having one end located adjacent the periphery of said shield member (8) and an opposite end located adjacent said substantially central portion of said shield member, a substantially central air passage (15) being defined between opposite ends of said first and second pluralities of ribs, said substantially central air passage (15) being in substantially unrestricted fluid communication with said generally U-shaped air passage channels (10), said substantially unrestricted air passage channels (10) substantially unrestrictedly opening to the periphery of said shield unit (8) and extending substantially unrestrictedly from at least said openings at said periphery of said shield unit to said substantially central air passage (15), said shield unit being coupled to said conduit (7) such that said substantially unrestricted air passage channels (10) are in substantially unrestricted air communication with the interior of said conduit (7) via said substantially central air passage (15) to provide substantially unrestricted flow of air from the periphery of said shield unit to the interior of said conduit (7) and to said mouthpiece (1), whereby said shield unit is adapted to be placed against a body portion of a user to provide substantially unrestricted open-ended air flow passages through said U-shaped air passage channels, said substantially central air passage and to said mouthpiece via said conduit whereby the body heat of the user heats cold air passing therethrough.

2. The cold weather breathing device of claim 1, wherein said valves comprise flap-type valves (3, 4), each valve comprising a pivotally mounted plate-like member which freely pivots from an open to a closed position responsive to air pressure caused by breathing of the user.

3. The cold weather device of claim 2, wherein said first flap-type valve is pivotally mounted at a lower portion thereof so that it falls due to gravity to an exhale position to block the air communication path between said mouthpiece and said conduit, and said second plate-like valve member (3) is pivotally mounted at the upper portion thereof so that it falls due to gravity to a closed position blocking said exhaust opening in an inhale position thereof.

4. The cold weather breathing device of claim 2, wherein at least one of said freely pivotable flap-type valves is angulated relative to the direction of air flow therethrough, to reduce the amount of force required to operate same.

5. The cold weather breathing device of claim 1 or 2, wherein said conduit (7) is flexible.

6. The cold weather breathing device of claim 5, wherein said conduit comprises a bellows (17).

7. The cold weather breathing device of claim 1 further comprising sealing means (13) coupled to said shield unit (8,9) for providing an air seal at the upper torso area of a user.

8. The cold weather breathing device of claim 1, wherein said valve housing (2) comprises a saliva catch (11) for retaining saliva in the exhaled air of a user.

9. The cold weather breathing device of claim 1, further comprising a layer of porous material (16) covering the ends of said ribs (9) which are remote from said shield member (8).

10. The cold weather breathing device of claim 9, wherein said layer (16) of porous material spans the spacing between said ribs (9).

11. The cold weather breathing device of claim 10, wherein said layer (16) of porous material comprises an air pervious fabric layer.

12. The cold weather breathing device of claim 1, wherein said mouthpiece (1), conduit (7) and shield unit (8,9) are all fabricated of flexible material.

13. The cold weather breathing device of claim 1, wherein said conduit comprises a bellows member (17)

to provide a high degree of relative movability between said mouthpiece (1) and said shield unit (8).

14. The cold weather breathing device of claim 1, wherein said shield unit further comprises an air opening at the bottom end thereof in air communication with said substantially central air passage (15) to provide still further air intake.

15. The cold weather breathing device of claim 1, wherein said ribs are substantially parallel with each other, thereby providing a plurality of said substantially unrestricted air passage channels in parallel with each other.

16. The cold weather breathing device of claim 1, comprising providing a spacing between ends of said ribs in the substantially central portion of said shield member to define said substantially central air passage (15).

17. The cold weather breathing device of claim 16, wherein said ribs define a plurality of said substantially unrestricted air passage channels (10) on each side of said substantially central air passage, said substantially unrestricted air passage channels defined between adjacent ribs being substantially perpendicular to said substantially central air passage.

18. The cold weather breathing device of claim 1, wherein said one ends of at least a plurality of said first plurality of ribs are located adjacent one of said opposite sides of said shield unit; and wherein said one ends of at least a plurality of said second plurality of ribs are located adjacent the other of said opposite sides of said shield unit.

19. A cold weather breathing device comprising:
a mouthpiece (1) which is insertable in the mount of a user and which substantially provides a seal to the mouth of the user;
a conduit (7) extending downwardly from said mouthpiece and in air communication with said mouthpiece;
a first valve (4) in air communication with said conduit (7) and mouthpiece (1) for providing air communication between said conduit and said mouthpiece when the user inhales, and for blocking said air communication between said conduit and mouthpiece when the user exhales;
an exhaust opening coupled to said mouthpiece (1) for exhausting exhaled air to the atmosphere;
a second valve (3) coupled between said exhaust opening and said mouthpiece (1) for providing air communication between said mouthpiece and said exhaust opening when the user exhales, and for blocking said air communication between said exhaust opening and mouthpiece when the user inhales; and
a shield unit having a top end, opposite sides, a bottom end and an intermediate portion, said shield unit including a substantially air impervious shield member (8) coupled to an end portion of said conduit (7) remote from said mouthpiece (1) and a first and second plurality of spaced apart projecting ribs (9) extending from one side of said shield member (8), adjacent ribs defining with said shield member (8) a plurality of elongated, generally U-shaped, substantially unrestricted air passage channels (10), said first plurality of ribs being one one side of said intermediate portion of said shield unit and said ribs of said first plurality of ribs having one end located adjacent the periphery of said shield member (8) and an opposite end located adjacent said intermediate portion of said shield member, said second plurality of ribs being on the other side of said intermediate portion of said shield unit and said ribs of said second plurality of ribs having one end located adjacent the periphery of said shield member (8) and an opposite end located adjacent said intermediate portion of said shield member, an intermediate air passage (15) being defined between opposite ends of said first and second pluralities of ribs, said intermediate air passage (15) being in substantially unrestricted fluid communication with said generally U-shaped substantially unrestricted air passage channels (10), said substantially unrestricted air passage channels (10) substantially unrestrictedly opening to the periphery of said shield unit (8) and extending substantially unrestrictedly from at least said openings at said periphery of said shield unit to said intermediate air passage (15), said shield unit being coupled to said conduit (7) such that said substantially unrestricted air passage channels (10) are in substantially unrestricted air communication with the interior of said conduit (7) via said intermediate air passage (15) to provide substantially unrestricted flow of air from the periphery of said shield unit to the interior of said conduit (7) and to said mouthpiece (1), whereby said shield unit is adapted to be placed against a body portion of a user to provide substantially unrestricted open-ended air flow passages through said U-shaped air passage channels, said intermediate air passage and to said mouthpiece via said conduit whereby the body heat of the user heats cold air passing therethrough.

20. The cold weather breathing device of claim 19, wherein said one ends of at least a plurality of said first plurality of ribs are located adjacent one of said opposite sides of said shield unit; and wherein said one ends of at least a plurality of said second plurality of ribs are located adjacent the other of said opposite sides of said shield unit.

21. The cold weather breathing device of claim 19, wherein said intermediate portion of said shield unit is a substantially central portion of said shield unit.

* * * * *